United States Patent [19]

Kaku et al.

[11] 4,355,184

[45] Oct. 19, 1982

[54] SYNTHESIS OF α, β-UNSATURATED-KETONES

[75] Inventors: Tsutomu Kaku; Kiyoshi Katsuura; Mikio Sawaki, all of Takaoka, Japan

[73] Assignee: Nippon Soda Company Limited, Tokyo, Japan

[21] Appl. No.: 257,639

[22] Filed: Apr. 27, 1981

[30] Foreign Application Priority Data

May 2, 1980 [JP] Japan .................................. 55/57953

[51] Int. Cl.³ ............................................. C07C 49/20
[52] U.S. Cl. .................................... 568/31; 568/388; 568/397
[58] Field of Search .......................... 568/31, 388, 397

[56] References Cited

U.S. PATENT DOCUMENTS

| | | | |
|---|---|---|---|
| 2,108,427 | 2/1938 | Boses . | |
| 3,466,334 | 9/1969 | Young et al. | 568/388 |
| 3,944,622 | 3/1976 | Okamoto et al. | 568/388 X |
| 4,283,348 | 8/1981 | Wheeler | 568/388 X |

FOREIGN PATENT DOCUMENTS 55-141429  5/1980  Japan .................................. 568/388

OTHER PUBLICATIONS

Lawesson et al., "Acta. Chem. Scand.", vol. 17, pp. 2216–2220 (1963).
Indian Journal of Chemistry", Chandrasekharan et al., vol. 16B, pp. 970–972.
Rupe et al., "Ber". vol. 40, pp. 4764–4777.
Becker et al., "Chem. Ber.", vol. 103, pp. 2077–2083 (1970).

Primary Examiner—Werren B. Lone
Attorney, Agent, or Firm—George B. Oujevolk

[57] ABSTRACT

α, β-unsaturated-ketones are synthesized by reacting with an aldehyde and an alkali metal salt of acetoacetic acid in the presence of an aliphatic secondary amine in the mixture of heterogeneous solvents producing an oil layer and a water layer.

3 Claims, No Drawings

SYNTHESIS OF α, β-UNSATURATED-KETONES

DETAILED DESCRIPTION OF THE INVENTION

The present invention is concerned with a new synthetic method of α, β-unsaturated-ketones. Said ketones are usable intermediates to manufacture medicines and pesticides, particularly, 6-ethylthio-3-heptene-2-on is used to manufacture a herbicide.

In known prior methods to manufacture said ketones, aldehydes is used as one of raw materials. However, those are not suitable methods to be employed for an industrial manufacturing method by reason of having some defects.

According to Ber. 40, 4764(1907), said ketones are synthesized by the aldol condensation with aldehydes and acetone. However, in the method, objected ketones are obtained in low yield without using aldehydes which have not α-position hydrogen atom, and, it have to use large excess acetone.

According to Indian J. Chem. Vol. 16B, 970–972(1978), said ketones are synthesized by a condensation with aldehydes and acetone in the presence of piperidine-acetic acid as the catalyst. In the method, large quantity of expensive catalysts and large excess acetone is used. Furthermore, in case of using easily dissociative aldehydes such as 3-ethylthiobutanal etc., objected ketones are obtained in very low yield by the decomposition of it.

According to Ber. 103, 2077(1970), said ketones are synthesized by reacting with aldehydes and Witting reagent which is produced by reacting with monochloroacetone or mono-bromoacetone and tri-phenylphosphine. In the method, Witting reagent is very expensive, and the waste treatment containing phosphines is very difficult.

According to Acta. Chem. Scand. 17, 2216–2220(1963), said ketones are obtained by heat decomposition of α,β-unsaturated-β'-ketoic acid esters using p-toluene sulfonic acid as the catalyst at high temperature, in which, α, β-unsaturated-β'-ketoic acid esters are synthesized by reacting with aldehydes and tert-butylacetoacetates. However, in the method, the producing reaction of said β'-ketoic acid esters takes long time, but the yield of the objected compound is low. Furthermore, in case of using easily dissociative aldehydes such as 3-ethylthiobutanal, the objected compound can not be almost obtained by the decomposition of it.

According to U.S. Pat. No. 2,108,427, said ketones are synthesized by reacting with aldehydes and diketone. However, the reaction takes long time, and objected ketones are obtained in low yield.

It is an object of the present invention to provide a new synthetic method of α, β-unsaturated-ketones, which is able to be employed for an industrial manufacturing process by reason of having the high yield of objected ketones under gentle reacting conditions.

These and other objects of the present invention will be become more apparent in the detailed description and examples which follow.

The present invention is a synthetic method of α, β-unsaturated-ketones, in which said ketones are synthesized by reacting with aldehydes having α-position hydrogen atom, and alkali metal salts of acetoacetic acid, in the presence of an aliphatic secondary amine in the mixture of heterogeneous solvents producing an oil layer and a water layer.

In the present invention, objected α, β- unsaturated-ketones of the synthesis are 3-alkene-2-ons having a following general formula [I],

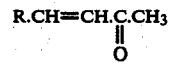
 [I]

wherein, R shows aldehyde residues of alkylaldehydes used as a raw material. Said alkylaldehydes are having α-position hydrogen atom, and shown as a following general formula [II],

R.CHO  [II]

wherein, said alkylaldehydes are streight or branched alkylaldehydes having 2 to 10 carbon atoms, such as ethanal, propanal, i-butanal, n-butanal, n-hexanal, n-octanal, n-caprylaldehyde, n-caprinealdehyde, etc., alkylthioalkylaldehydes, such as methylthioethanal, ethylthioethanal, propylthioethanal, 3-ethylthiopropanal, 3-butylthiopropanal, 2-methylthiopropanal, 2-propylthiopropanal, 3-ethylthiobutanal, 3-butylthiobutanal, 2-methylthiobutanal, 2-propylthiobutanal etc., alkylsulfinylalkylaldehydes, such as methylsulfinylethanal, ethylsulfinylethanal, 3-ethylsulfinyl propanal, 3-propylsulfinyl propanal, 2-propylsulfinylpropanal, 2-butylsulfinylpropanal, 3-methylsulfinylbutanal, 3-ethylsulfinylbutanal, 2-ethylsulfinylbutanal, 2-propylsulfinylbutanal, etc., alkylsulfonylaldehydes, such as methylsulfonylethanal, 3-ethylsulfonylpropanal, 2-propylsulfonylpropanal, 3-ethylsulfonylbutanal, 3-butylsulfonylbutanal, 2-methylsulfonylbutanal, etc., phenyl- or substituted phenylalkylaldehydes, such as, benzyl aldehyde, 2-(4'-ethylphenyl)ethanal, 2-(4'-methoxyphenyl)ethanal, 3-(4'-methylphenyl)propanal, 3-(2',5'-dimethylphenyl)propanal, 3-(4'-chlorophenyl)propanal, 2-(4'-ethylphenyl)propanal, 2-(4'-methoxyphenyl)propanal, 2-(2',4'-dichlorophenyl)propanal, 3-(4'-methylphenyl)butanal, 3-(2',5'-dimethylphenyl)butanal, 3-(4'-chlorophenyl)butanal, 2-(4'-ethylphenyl)butanal, 2-(4'-methoxyphenyl)butanal, 2-(2',4'-dichlorophenyl)butanal, etc., phenylthio- or substituted phenylthioaldehydes, such as phenylthioethanal, (2',5'-dimethylphenylthio)ethanal, 3-(4'-methylphenylthio)propanal, 3-(4'-methoxyphenylthio)propanal, 2-(4'-ethylphenylthio)propanal, 2-(4'-chlorophenylthio)propanal, 3-(4'-ethylphenylthio)butanal, 3-(2',4'-dichlorophenylthio)butanal, 2-(4'-methylphenylthio)butanal, 2-(4'-chlorophenylthio)butanal, etc., phenylsulfinylalkylaldehydes or phenylsulfonylalkylaldehydes such as, 3-(4'-chlorophenylsulfinyl)propanal, 3-phenylsulfonylpropanal, 3-(4'-methylphenylsulfonyl)butanal, 2-(4'-chlorophenylsulfonyl)butanal, 2-(4'-chlorophenylsulfonyl)butanal, etc., or benzylthioalkylaldehydes, such as 3-benzylthio propanal, etc.

Another used raw material is alkali metal salts of acetoacetic acid having a following general formula [III],

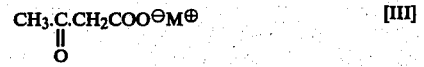
 [III]

wherein, M⊕ shows alkali metals, such as sodium, potassium, etc. Said alkali metal salts of acetoacetic acid are easily obtained as an aqueous solution by hydrolysis of diketone or acetoacetates using caustic alkali, such as caustic soda, caustic potash etc., and the obtained alkali metal salts of acetoacetic acid aqueous solution is used in the present invention.

The reaction between said aldehydes and said alkali metal salts of acetoacetic acid is made in the presence of an aliphatic amine in the mixture of heterogeneous solvents producing an oil layer and a water layer, by the following reaction equation,

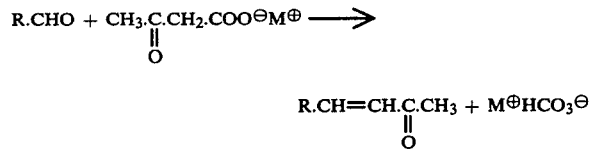

and, objected ketones and alkali metal salts of bicarbonate are produced.

In the said reaction, it is used as the catalyst that an amine is selected from the aliphatic secondary amines group, for example, a cyclic aliphatic secondary amines, such as pyrrolidine, morpholine, piperazine piperidine, substituted piperidine, e.g. 3-methylpiperidine, 3-ethylpiperidine, 4-methylpiperidine, 4-ethylpiperidine, 1,3-di-piperidylpropane, etc., and N-alkyl-n-alkylamines, such as di-methylamine, di-ethylamine, di-n-propylamine, di-n-butylamine, N-methyl-n-butylamine, N-ethyl-n-butylamine, N-methyl-n-amylamine, N-methyl-n-hexylamine, N-methyl-n-heptylamine, N-methyl-n-octylamine, N-ethyl-n-nlaurylamine, etc. These amines act selectively the aldehyde to the alkali metal salt of acetoacetic acid. However, it is undesirable to use aliphatic secondary amines such as di-iso-propylamine, di-cyclohexylamine, by reason of indicating the steric hindrance.

The said reaction is made in the mixture of heterogeneous solvents producing the oil layer and the water layer. The said oil layer is produced by using an insoluble or slightly soluble organic solvent in water, for example, chlorinated hydrocarbons such as di-chloromethane, chloroform, di-chloroethane, etc., and alomatic hydrocarbons such as benzene, toluene, xylene, etc.

In the present invention, the objected ketone is obtained by embodiments shown as follows.

More than 0.005 mol per mol of aldehyde, preferably, 0.02 to 0.08 mol per mol of aldehyde of an amine as the catalyst is added into the aqueous solution containing 1.0 to 1.5 mol per mol of aldehyde, preferably, 1.1 to 1.3 mol per mol of aldehyde of an alkali metal salt of acetoacetic acid obtained by the above said procedure, and then, the resulted solution is adjusted to the pH range at 6.0 to 8.0 by adding an inorganic acid such as hydrochloric acid etc.

A raw aldehyde and 100–500 ml per mol of an organic solvent are added into the above said solution containing the alkali metal salt of acetoacetic acid and the catalyst.

Then, the resulted mixture is stirred for 2 to 7 hours, under conditions of the atomspheric pressure and the temperature at 10° to 50° C., preferably, 20° to 40° C.

During the reaction, the pH range is kept at 6.0 to 8.0 by dropping an inorganic acid such as hydrochloric acid, etc.

Above said reaction conditions are slightly varied by the kind and quantity of using aldehydes, amines, and organic solvents. However, the reaction using numerial values without the above said limited range is undesireble by reason of lowering the yield of the objected ketone.

After the reaction, in case of finding crystals of alkali metal salt of bicarbonate, said crystals are decomposed by adding an inorganic acid such as hydrochloric acid, etc., and then, produced inorganic compounds are dissolved in the water layer. Then, the reaction mixture is separated to the oil layer containing the produced object ketone and the water layer containing the produced inorganic compound, by using an ordinary method such as decantation, filteration etc. The objected ketone is obtained by concentrating and then distillating the above separated oil layer.

In the method according to the present invention, synthesized $\alpha$, $\beta$-unsaturated ketones are streight or branched 3-alkene-2-ons having 5 to 12 carbon atoms such as 3-pentene-2-on, 3-hexen-2-on, 5-methyl-3-hexene-2-on, 3-hetpene-2-on, 3-octene-2-on, 3-nonene-2-on, 3-undecene-2-on, 3-tridecene-2-on etc., alkylthio-3-alkene-2-ons, such as 5-methylthio-3-pentene-2-on, 5-ethylthio-3-pentene-2-on, 5-propylthio-3-pentene-2-on, 6-ethylthio-3-hexene-2-on, 6-propylthio-3-hexene-2-on, 6-butylthio-3-hexene-2-on, 5-methylthio-3-hexene-2-on, 5-propylthio-3-hexene-2-on, 6-ethylthio-3-heptene-2-on, 6-butylthio-3-heptene-2-on, 5-methylthio-3-heptene-2-on, 5-butylthio-3-heptene-2-on, etc., alkylsulfinyl-3-alkene-2-ons and alkylsulfonyl-3-alkene-2-ons, such as 6-methylsulfinyl-3-hexene-2-on, 6-propylsulfinyl-3-hexene-2-on, 5-ethylsulfinyl-3-hexene-2-on, 5-butylsulfinyl-3-hexene-2-on, 6-ethylsulfinyl-3-heptene-2-on, 6-butylsulfinyl-3-heptene-2-on, 5-methylsulfinyl-3-heptene-2-on, 5-propylsulfinyl-3-heptene-2-on, 6-ethylsulfonyl-3-hexene-2-on, 5-propylsulfonyl-3-hexene-2-on, 6-methylsulfonyl-3-heptene-2-on, 5-butylsulfonyl-3-heptene-2-on, etc., phenyl-3-alkene-2-ons, such as 5-phenyl-3-pentene-2-on, 5-(2',4'-dimethylphenyl)-3-hexene-2-on, 5-(4'-ethylphenyl)-3-hexene-2-on, 5-(4'-chlorophenyl)-3-hexene-2-on, 6-(4'-methylphenyl)-3-heptene-2-on, 6-(2',4'-dichlorophenyl)-3-heptene-2-on, 5-(4'-ethylphenyl)-3-heptene-2-on, 5-(4'-chlorophenyl)-3-heptene-2-on, etc., phenylthio-3-alkene-2-ons, such as 5-phenylthio-3-pentene-2-on, 5-(4'-ethylphenylthio)-3-pentene-2-on, 5-(4'-chlorophenylthio)-3-pentene-2-on, 6-(4'-methylphenylthio)-3-hexene-2-on, 6-(2',5'-dimethylphenylthio)-3-hexene-2-on, 6-(2',4'-dichlorophenylthio)-3-hexene-2-on, 5-(4'-methoxyphenylthio)-3-hexene-2-on, 5-(4'-chlorophenylthio)-3-hexene-2-on, 6-(4'-ethylphenylthio)-3-heptene-2-on, 6-(4'-chlorophenylthio)-3-heptene-2-on, 5-(2',5'-dimethylphenylthio)-3-heptene-2-on, 5-(2',4'-dichlorophenylthio)-3-heptene-2-on, etc., phenylsulfinyl-3-alkene-2-ons and phenylsulfonyl-3-alkene-2-ons, such as 6-(4'-chlorophenylsulfinyl)-3-hexene-2-on, 6-phenylsulfonyl-3-hexene-2-on, 6-(4'-methylsulfonyl)-3-heptene-2-on, 6-(4'-chlorophenylsulfonyl)-3-heptene-2-on, or benzylthio-3-alkene-2-ons such as 6-benzylthio-3-pentene-2-on, etc.

The present invention provides a new synthetic method of $\alpha$, $\beta$-unsaturated-ketones which is appropriate to be employed as an industrial manufacturing of it.

Namely in the method, an objected ketone is obtained in more than 80% of yield under gentle reaction conditions such as the atmospheric pressure and the room temperature, and further the objected ketone can be easily separated from the reaction mixture.

Subsequently, the present invention is more minutely explained by referring to Examples as follows, however, the examples are intended to illustrate the invention and are not to be construed to limit the scope of the invention.

EXAMPLE 1

Production of sodium-acetoacetic acid aqueous solution.

In the reactor having 300 ml volume, 0.39 mol of methylacetoacetate and 54.6 gr of water were put in it, and then, 54.6 gy of 30% caustic soda aqueous solution was added into the mixture. During the addition of caustic soda, the temperature was kept at below 35° C. by in water bath.

The mixture was kept at 30° to 35° C. for 6 hours with stirring, and carried out hydrolysis reaction. By the pH of the reaction mixture was adjusted to 8.3 by addition of concentrated hydrochloric acid, the sodium-acetoacetic acid aqueous solution was obtained.

Production of $\alpha, \beta$- unsaturated-ketone 0.0225 mol of di-n-butylamine was added into so obtained sodium-acetoacetic acid aqueous solution, and then the pH of the mixture was adjusted to 6.0 by adding concentrated hydrochloric acid. 60 ml of toluene and 0.3 mol of n-caprinealdehyde were added into the obtained mixture, and stirred for 4 hours keeping at 30° C. After the reaction, concentrated hydrochloric acid was dropped slowly into the mixture to decompose crystallized sodium bicarbonate.

Then, the oil layer and the water layer were separated from the reaction mixture by decantation.

The oil layer was concentrated, and then distillated under vacuum, and 51.8 gr of colorless oily product having boiling point of 106° to 112° C. at 0.8 torr. (mmHga) and $n_D^{21}$ 1.4555 was obtained.

The said oily product was identified by the gas-chromatograph as 3-tridecene-2-on. The purity of 3-tridecene-2-on was 97.9%, and the yield from aldehyde was 86.2%.

EXAMPLE 2–16

Example 1 was repeated by using changed aldehyde, amine and other conditions according to the Table 1.

The results including Example 1 are shown in the Table 1.

TABLE 1

| No. of Example | Raw Aldehyde R.CHO | Product R.CH=CH.C.CH$_3$ ‖ O (R—) | Amines as catalyst | Mol Ratio Amine/ aldehyde | Reaction temp. (°C.) time (hr) | Yield (%) | Remarks | |
|---|---|---|---|---|---|---|---|---|
| 1 | CH$_3$(CH$_2$)$_8$— | | di-n-butylamine | 0.075 | 30 / 4 | 86.2 | b.p. 106–112° C. at 0.8 torr $n_D^{21}$ 1.4555 | (Calculated) C: 79.53 H: 12.32 (Analized) C: 79.39 H: 12.32 |
| 2 | CH$_3$(CH$_2$)$_6$— | | di-n-propylamine | 0.05 | 30 / 4 | 91.5 | b.p. 81.5–83.5° C. at 1 torr $n_D^{20.51}$ 1.4528 | |
| 3 | CH$_3$(CH$_2$)$_4$— | | N—ethyl-n-butyl-amine | 0.05 | 30 / 4 | 90.3 | b.p. 81–82.5° C. at 6 torr $n_D^{19.5}$ 1.4493 | |
| 4 | CH$_3$(CH$_2$)$_3$— | | pyrrolidine | 0.05 | 30 | 92.0 | ** | |
| 5 | CH$_3$(CH$_2$)$_2$— | | N—methyl-n-butylamine | 0.05 | 30 / 5 | 93.1 | ** | |
| 6 | CH$_3$.CH$_2$— | | piperidine | 0.05 | 30 / 5 | 83.1 | b.p. 42–42.5° C. at 14 torr $n_D^{22.5}$ 1.4410 | |
| 7 | CH$_3$.CH$_2$.S.CH.CH$_2$— \| CH$_3$ | | 3-methyl-piperidine | 0.075 | 30 / 6 | 90.6 | b.p. 84–86° C. at 0.5 torr $n_D^{14}$ 1.5010 | (Calculated) C: 62.74 H: 9.36 S: 18.61 (Analized) C: 62.68 H: 9.35 S: 18.96 |
| 8 | CH$_3$.CH$_2$.S.CH.CH$_2$— \| CH$_3$ | | 3-methyl-n-piperidine | 0.05 | 30 / 5 | 96.3 | ** | |
| 9 | CH$_3$.CH$_2$.S.CH.CH$_2$— \| CH$_3$ | | N—methyl-n-hexyl-amine | 0.035 | 30 / 5 | 95.6 | ** | |
| 10 | CH$_3$.CH$_2$.S.CH.CH$_2$— \| CH$_3$ | | N—methyl-n-heptylamine | 0.05 | 30 / 2.5 | 94.2 | ** | |
| 11 | 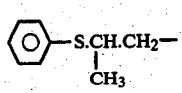—S.CH.CH$_2$— \| CH$_3$ | | N—ethyl-n-butylamine | 0.05 | 30 / 5 | 91.7 | ** | |
| 12 | CH$_3$—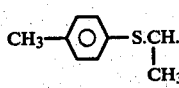—S.CH.CH$_2$— \| CH$_3$ | | 3-methyl-piperidine | 0.05 | 30 / 5 | 89.8 | ** | |

TABLE 1-continued

| No. of Example | Raw Aldehyde R.CHO | Product R.CH=CH.C.CH₃ ‖ O (R—) | Amines as catalyst | Mol Ratio Amine/ aldehyde | Reaction temp. (°C.) time (hr) | Yield (%) | Remarks |
|---|---|---|---|---|---|---|---|
| 13 | 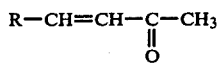 — S.CH.CH₂— / CH₃ | | N—methyl-hexyl-amine | 0.05 | 30 / 5 | 88.0 | ** |
| 14 | CH₃.CH₂.SO₂.CH.CH₂— / CH₃ | | N—methyl-hexyl-amine | 0.05 | 30 / 5 | 90.5 | ** |
| 15 | CH₃—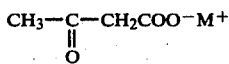—SO₂.CH.CH₂— / CH₃ | | pyrrolidine | 0.05 | 30 / 5 | 85.5 | ** |
| 16 | CH₃.CH₂.S.CH— / CH₃—CH₂ | | morpholine | 0.075 | 30 / 5 | 85.0 | ** |

Note:
*In Examples of No. 1, No. 9, No. 10 and No. 13, toluene was used as organic solvent, and in other Examples, chloroform was used.
**Identified by gas-chromatography.

What is claimed is:

1. A method of synthesis of α, β-unsaturated-ketones having a following general formula:

$$R-CH=CH-\underset{\underset{O}{\|}}{C}-CH_3$$

wherein, R is straight or branched alkyl group having 1 to 9 carbon atoms, alkylthioalkyl group, alkylsulfinylalkyl group, alkylsulfonylalkyl group, phenyl-or substituted phenylalkyl group, phenylthio- or substituted phenylthioalkyl group, phenylsulfinyl- or substituted phenylsulfinylalkyl group, phenylsulfonyl- or substituted phenylsulfonylalkyl group, or benzylthioalkyl group, in which the said ketones are synthesized by reacting with aldehydes having α-positing hydrogen atom shown as a following general formula:

R.CHO wherein, R is the same as the above definition, and alkali metal salts of acetoacetic acid having a following general formula:

$$CH_3-\underset{\underset{O}{\|}}{C}-CH_2COO^-M^+$$

wherein, M⁺ is sodium ion or potassium ion, in the presence of an aliphatic secondary amine, in mixed heterogeneous solvents with a water and an organic solvent which is able to produce a water layer and an oil layer by decantation, under conditions of atomospheric pressure and the temperature at 10° to 50° C., preferably, 20° to 40° C.

2. A method as claimed in claim 1 wherein the amine is selected from the group consisting of cyclic aliphatic secondary amines and N-alkyl-n-alkylamines.

3. A method as claimed in claim 1 wherein the organic solvent is selected from the group consisting of di-chloromethane, chloroform, di-chloroethane, benzene, toluene and xylene.